(12) United States Patent
Ruhnke

(10) Patent No.: US 10,184,814 B2
(45) Date of Patent: Jan. 22, 2019

(54) METHOD AND APPARATUS FOR DETECTING STAGNANT WATER

(71) Applicant: Neoperl GmbH, Muellheim (DE)

(72) Inventor: Christof Ruhnke, Berlin (DE)

(73) Assignee: Neoperl GmbH, Muellheim (DE)

( * ) Notice: Subject to any disclaimer, the term of this patent is extended or adjusted under 35 U.S.C. 154(b) by 137 days.

(21) Appl. No.: 14/978,600

(22) Filed: Dec. 22, 2015

(65) Prior Publication Data

US 2016/0202094 A1   Jul. 14, 2016

(51) Int. Cl.
| | |
|---|---|
| *G01F 1/05* | (2006.01) |
| *F03B 13/10* | (2006.01) |
| *G01N 33/18* | (2006.01) |
| *E03C 1/10* | (2006.01) |
| *F24D 17/00* | (2006.01) |

(52) U.S. Cl.
CPC ................ *G01F 1/05* (2013.01); *E03C 1/10* (2013.01); *F03B 13/10* (2013.01); *F24D 17/0073* (2013.01); *G01N 33/18* (2013.01); *E03C 2201/40* (2013.01)

(58) Field of Classification Search
CPC .. G01F 1/05; G01F 1/00; G01N 33/18; G01N 33/00; F03B 13/10; F03B 13/00
USPC ............................................. 73/861.77, 861
See application file for complete search history.

(56) References Cited

U.S. PATENT DOCUMENTS

| | | | | |
|---|---|---|---|---|
| 5,079,495 A | * | 1/1992 | Yasuo ..................... | E03D 5/105 320/101 |
| 2007/0108056 A1 | | 5/2007 | Nyberg et al. | |
| 2009/0277516 A1 | | 11/2009 | Winkler et al. | |
| 2011/0203364 A1 | * | 8/2011 | Staake ................ | F24D 19/1063 73/198 |
| 2014/0107835 A1 | | 4/2014 | Biasi et al. | |
| 2014/0312253 A1 | | 10/2014 | Gan | |

FOREIGN PATENT DOCUMENTS

| | | |
|---|---|---|
| DE | 690 00 906 T2 | 6/1993 |
| DE | 44 10 993 A1 | 10/1995 |
| DE | 10 2005 060 890 A1 | 7/2006 |
| DE | 10 2007 009 007 A1 | 8/2008 |
| DE | 10 2008 039 272 A1 | 2/2010 |
| DE | 10 2014 104 393 A1 | 10/2014 |
| DE | 10 2014 018 590 A1 | 6/2015 |
| EP | 0 675 234 A1 | 10/1995 |
| EP | 2 762 646 A1 | 8/2014 |

OTHER PUBLICATIONS

Grohe AG, DE 10 2014 018 590, English Machine Translation of DE 10 2014 018 590, Abstract, Description and Claims. Obtained on Jan. 10, 2018, pp. 1-23. (Year: 2018).*

* cited by examiner

*Primary Examiner* — Christine T Mui
(74) *Attorney, Agent, or Firm* — Fay Sharpe LLP

(57) ABSTRACT

A method of detecting stagnant water includes flowing a water in a pipe and producing electrical energy via the flow of the water. The electrical energy is stored in an energy store. A change of state of the energy store is detected and information about possible stagnation of the water is obtained from the change of state of the energy store. An apparatus for detecting stagnant drinking water includes a generator for producing electrical energy, an energy store for storing that energy, a control and analysis unit which detects the charge state of the energy store and a signal transmitter which emits a signal depending on the charge state of the energy store.

13 Claims, 1 Drawing Sheet

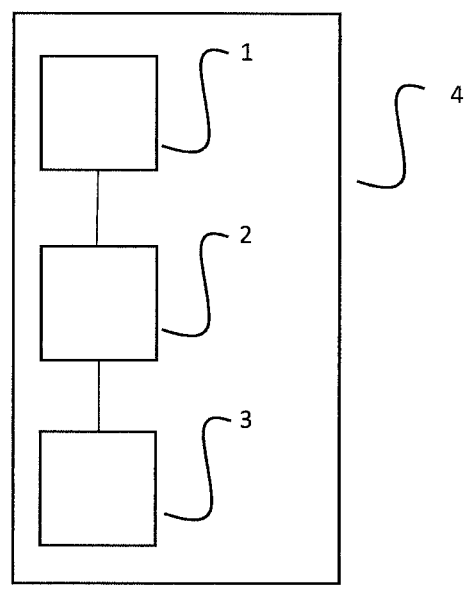

METHOD AND APPARATUS FOR DETECTING STAGNANT WATER

BACKGROUND

The invention relates to a method and an apparatus for detecting stagnant drinking water.

Stagnant water is to be understood as water which is stationary for a certain period of time in a pipe section. Stagnant water occurs when water is not removed (drawn off) for more than a certain period of time.

After only a few hours the formation of a biofilm can occur in stagnant water as a result of chemical, physical and microbial processes on the inner surface of the pipe section in question. Microbes, which multiply in a biofilm, reach the consumer when water is removed. A health risk to the consumer can result from this.

Pipe sections of e.g. faucets, conduits, shower hoses and tap outlets are affected by microbial contamination. In order to prevent or reduce microbial contamination in pipe sections, ring mains are known from the prior art from which relatively short feed lines go off to the water removal points. The advantage of such a construction is that when drawing off from each water removal point the water in the ring main is moved so that the residence time of the water in the ring main is low and stagnant water occurs only in the relatively short feed lines. The latter is vented by a flushing process before the drinking water (from the ring main) can be used. Ring mains are expensive and cannot be implemented universally.

Precautions can also be taken as regards materials which reduce microbial formation. In particular, materials are known from the prior art which reduce the risk of the formation of a biofilm.

The risk of using microbially contaminated drinking water can basically be reduced by allowing the water to run for a time before drawing off the drinking water provided for use.

The pipe is thus flushed and potentially stagnant water discharged. Depending on the length of the water supply pipe, the running time of the water is up to a few minutes.

The method described above has proved in practice to be satisfactory. However, discharging unused water for a long period of time is environmentally unfriendly, particularly if, for reasons of safety, the water is discharged for longer than would actually be necessary.

Practice shows also that it is frequently not clear before using a drinking water tap connection whether the backed up water is stagnant water or not. The consumer frequently provides security by basically allowing the water to run for a relatively long period of time, regardless of the degree of stagnation of the water, before it is drawn off for its actual use. The result is unnecessary water wastage.

This is where the invention comes into play.

It is the object of the invention to detect stagnant water whilst simultaneously reducing unnecessary water consumption.

BRIEF SUMMARY

In order to solve this object, the above is characterised in accordance with the invention in that
that electrical energy is produced in a pipe section by flowing water,
that the electrical energy is stored in an energy store,
that the charge state of the energy store is detected, and
that information about possible stagnation of the drinking water is obtained from the charge state of the energy store.

The invention combines a number of advantages. One advantage resides in that electrical energy is produced by flowing water. No separate energy source is thus necessary. A further, substantial advantage of the invention resides in the fact that information can be obtained from the charge state of the energy store as to whether stagnant water is present or not. In particular, the invention makes use of a discharged energy store in order to obtain the information from it that the water in the pipe section is stagnant water.

The energy store is preferably so selected that its discharge time is shorter than the time in which the water is considered subjectively or objectively to be stagnant water. The discharge time is, for instance, less than 12 hours, preferably less than 6 hours. Depending on the application, drinking water is defined as stagnant water when water, is stationary on its travel in the pipe in question for longer than 4 hours. Such conditions are to be found, in particular, in medical installations, such as hospitals. Against this background, it can be convenient if the discharge time is less than 4 hours.

As indicated above, the invention can find application in public institutions, such as hospitals, residential homes for the elderly and care homes or schools and also in private households.

The degree of freshness of the drinking water is preferably derived from its stagnation. It is thus preferably possible that, on the one hand, it can be ensured that the water which is drawn off is fresh and that, on the other hand, unnecessary water is not wasted (by unnecessary flushing of the pipe).

It should be mentioned at this point that in the context of the invention the term degree of freshness is to be understood, for instance, merely as the states "fresh" or "not fresh". In a further embodiment of the invention, however, graduated degrees of freshness can also be determined. These are preferably derived from a partially discharged energy store. Thus when the energy store has a residual charge, it can be derived from this that the water which is drawn off is "not fresh".

The degree of freshness of the water is advantageously indicated acoustically and/or visually. The degree of freshness is thus rapidly ascertainable for the user. "Fresh" water can, for instance, be indicated with a light, which is e.g. green or blue. Additionally or alternatively, an acoustic signal or a series of acoustic signals can occur. With "not fresh", that is to say stagnant, water, there is preferably no acoustic and/or visual indication.

Alternatively and also regarded as advantageous is if stagnant water is indicated visually. There can, for instance, be a red signal. The water is thereby indicated as "fresh" if no signal is given. In this variant, a signal is thus a warning signal for stagnant water.

As soon as the water is stationary for a certain, preferably predetermined, period of time in the pipe section, the energy store discharges. If the pipe or pipe section is then flushed, the energy store charges up again. If the energy store is discharged, the drinking water is indicated as "fresh" after a certain, preferably predetermined, running time. In this connection, a number of scenarios are possible. For instance, the water is indicated as "fresh" when the energy store is fully charged or has reached a predetermined charge state. The pre-setting of a specific running time, for instance 1 minute, is also possible.

It is regarded as preferred if the running time is adjustable. The method is thereby matchable to its specific place of usage. If it is, for instance, known that the pipe section to the water removal point is long, the running time is selected to be long. With a short pipe section, for instance a short feed pipe, the running time can be maintained relatively short. As a result of the adjustability, the amount of flushing water, that is to say of stagnant water which is run off, can be maintained as small as possible. Such a water saving is environmentally friendly.

It can in practice be provided that the running time is continuously adjustable. Alternatively, the running time is adjustable in predetermined steps.

The adjustability described above offers a simple possibility of matching the method in accordance with the invention to environmental conditions. A certain knowledge of the location is thereby a prerequisite. More precise adjustability can be provided if, in order to determine the running time, water is permitted to run off once, the water temperature is measured during the running off process and the running off time is determined on the basis of the change in water temperature. The background to this possibility for adjustment is based on the fact that when the water is stationary its temperature matches the ambient temperature. This is, for instance, the temperature of the room through which the pipe in question runs. In north and west European countries, the room temperature is higher than the temperature of the "fresh" water coming from the central water supply. On the other hand, countries in warmer regions are known, in which the room temperature can be lower as a result of airconditioning. As soon as a certain temperature change occurs, it can be inferred that fresh water is available at the removal point. In practice, the temperature measurement can be effected, for instance, manually, that is to say by feeling the temperature. As soon as the sensed water temperature subjectively changes, the time period is thus determined, after which the water is "fresh". The running of time thus determined can be used for future water removal processes.

As regards the energy store, those stores may be considered which store electrical energy and discharge within a suitable period of time. An accumulator can, for instance, be used. Since the discharge times of accumulators are long, as determined by their construction, additional electrical components, (such as, for instance, an optical indicator) can be provided, which are powered by the accumulator. The discharge time is thereby shortened.

It is considered to be particularly advantageous if the energy store is constructed in the form of a capacitor. Such capacitors can be maintained structurally very small. Furthermore, capacitors exhibit suitable charging and discharging characteristics.

The object is further solved by an apparatus for detecting stagnant water including
  a generator for producing electrical energy,
  an energy store for storing electrical energy,
  a control and analysis unit, which detects the charge state of the energy store, and
  a signal transmitter, which emits a signal in dependence on the charge state of the energy store.

The generator is preferably driven by a turbine. The turbine is advantageously a component of the apparatus. It is conveniently arranged in the pipe section.

The control and analysis unit detects the charge state of the energy store. The signal transmitter emits a signal in dependence on the charge state of the energy store. When the energy store is empty, the signal transmitter emits no signal. When the energy store is full, the signal transmitter preferably emits a signal, preferably one which shows the water to be "fresh".

The signal is advantageously an optical signal. The signal can be a permanent or a flashing light signal. It is, for instance, possible that "fresh" water is indicated by a first, for instance permanent, light signal. Depending on the discharge time of the energy store, stagnant water is indicated with a second light signal, for instance of a different colour. As explained above, when the energy store is discharged there is no signal, whereby it can additionally advantageously be provided that during the charging of the energy store, that is whilst water which is still stagnant is running off, a corresponding signal is emitted, which can be different to the first signal, which represents "fresh" water.

It is also regarded as advantageous when stagnant water is indicated and not "fresh" water. In normal operation, that is to say when "fresh" water is present at the removal point, there is advantageously no signal. When, however, the energy store is empty and stagnant water is removed, the electrical energy of the generator is used to emit a signal that the water is stagnant water. The signal is, for instance, red.

The apparatus in accordance with the invention is simple and composed of few components. It is considered to be particularly advantageous if the apparatus is in the form of an end or intermediate member for a water outlet, particularly for a water faucet. The apparatus in accordance with the invention can thus also be incorporated as a retrofit component. More substantial alteration of a standard faucet is not necessary for this purpose. In this connection, it is also advantageous if the energy store is constructed in the form of a capacitor which permits a particularly small overall size of the apparatus in accordance with the invention and its accommodation in the end or intermediate member.

In a further embodiment of the invention it is proposed that an input device is provided, by means of which the control and analysis unit can be supplied with a time period. The time period can be that time which the stagnant water requires to run out of a pipe section until it is fresh. With the energy store discharged, with an appropriate input into the control and analysis unit the water is only indicated as "fresh" after the time period. As explained above, the information relating to "fresh" water can be provided by an active (e.g. optical or acoustic) signal or by the fact that no signal is emitted. In the latter case, a signal is present when the water is stagnant water.

A temperature sensor can additionally be provided, which provides additional monitoring of the water. For instance, the stagnant water, which is running off, can be monitored as to whether, optionally after a pre-set time period, after a temperature change the water temperature is constant.

BRIEF DESCRIPTION OF THE DRAWINGS

The invention will be described in more detail below with reference to the attached drawing in conjunction with the described exemplary embodiment. The drawing shows:

FIG. 1: a schematic view of the basic construction of a detection apparatus in accordance with the invention.

DETAILED DESCRIPTION

The apparatus in accordance with the invention includes a generator 1, which is arranged in a pipe section (not shown). The generator 1 is driven by a turbine located in the pipe section through which water flows and thus produces electrical energy. The energy is stored in an energy store 2, which can be constructed, for instance, in the form of a capacitor. Reference numeral 3 designates a signal transmitter, which produces, for example, an optical signal when fresh water is at the tap connection. The components 1, 2 and 3 can be accommodated in a unit 4, which is, for instance, an end member or an intermediate member 4 for a water outlet.

The invention claimed is:

1. A method of detecting stagnant water, comprising:
producing electrical energy in a pipe section by flowing a drinking water in the pipe section,
storing the electrical energy in an energy store,
discharging the energy store after a predetermined time period if the drinking water remains stationary in the pipe section, wherein the energy store is selected that a discharge time is shorter than a time period after which the drinking water is considered to be stagnant,
detecting a charge state of the energy store via a control and analysis unit, and
obtaining information about a stagnation condition of the drinking water from the charge state of the energy store.

2. A method as claimed in claim 1, further comprising deriving information about a degree of freshness of the drinking water from information about the stagnation condition of the drinking water.

3. A method as claimed in claim 2, further comprising indicating the degree of freshness of the drinking water by at least one of acoustically and visually.

4. A method as claimed in claim 2, characterised in that when the energy store is discharged the drinking water is indicated, after a predetermined discharge time, as being "fresh".

5. A method as claimed in claim 4, characterised in that the discharge time is adjustable.

6. A method as claimed in claim 4, characterised in that determining the discharge time comprises, discharging the drinking water once, measuring a water temperature during the step of discharging and setting the discharge time on the basis of a change in water temperature.

7. A method as claimed in claim 1, characterised in that the energy store is constructed in the form of a capacitor.

8. A method of detecting stagnant water comprising:
flowing water in a pipe;
producing electrical energy via the flow of the water,
storing the electrical energy in an energy store;
fully discharging the electrical energy from the energy store after a predetermined time period if the water remains stationary in the pipe, wherein the energy store is selected that a discharge time is shorter than a time period after which the drinking water is considered to be stagnant;
detecting a charge state of the energy store via a control and analysis unit; and
wherein information about a stagnation condition of the water is obtained from the charge state of the energy store.

9. The method of claim 8 wherein the water is a drinking water.

10. The method of claim 8 further comprising detecting a temperature of the water and setting the discharge time on the basis of a change in water temperature.

11. The method of claim 8 further comprising indicating a degree of freshness of the water by at least one of acoustically and visually.

12. The method of claim 8 further comprising deriving information about a degree of freshness of the water from information about a stagnation condition of the water.

13. A method of detecting stagnant drinking water comprising:
providing a unit on an end member or an intermediate member of an outlet of a water pipe, the unit including a generator, an energy store and a signal transmitter,
flowing water in the water pipe;
producing electrical energy via the generator;
storing the electrical energy in the energy store;
fully discharging the electrical energy from the energy store after a predetermined time period if the water remains stationary in the water pipe, wherein the energy store is so selected that its discharge time is shorter than a time period after which the drinking water is considered to be stagnant;
detecting a charge of state of the energy store via a control and analysis unit; and
indicating a condition of the water via the signal transmitter in dependence on the charge state of the energy store.

* * * * *